US006284754B1

(12) United States Patent
Boddé et al.

(10) Patent No.: US 6,284,754 B1
(45) Date of Patent: Sep. 4, 2001

(54) PHARMACEUTICAL COMPOSITIONS CONTAINING 1-OLEYLAZACYCLOHEPTAN-2-ONE AS ENHANCING AGENT OF TRANSPORT ACROSS BIOLOGICAL MEMBRANES

(75) Inventors: Henri Ernest Boddé, Alphen a/d Rijn; Johanna Aaltje Bouwstra; Maria Helène Ponec, both of Leiden; Ferdinand Spies, Oegstgeest, all of (NL); Klaus Sandrock, Langenfeld (DE); Johannes Brussee, Rijnsburg (NL)

(73) Assignee: Schwarz Pharma AG, Monheim (DE)

( * ) Notice: Subject to any disclaimer, the term of this patent is extended or adjusted under 35 U.S.C. 154(b) by 0 days.

(21) Appl. No.: 08/004,603

(22) Filed: Jan. 14, 1993

(30) Foreign Application Priority Data

Jan. 20, 1992 (EP) .................................................. 92200159

(51) Int. Cl.[7] .................................................. A61K 31/55
(52) U.S. Cl. ...................................... 514/212.03; 540/485
(58) Field of Search ............................... 514/212, 212.03; 540/485

(56) References Cited

U.S. PATENT DOCUMENTS 3,989,816 11/1976 Rajadhyaksha ...................... 540/485
4,310,525 1/1982 Nelson ................................ 540/485
4,415,563 * 11/1983 Rajadhyaksha ...................... 514/212
4,855,294 * 8/1989 Patel et al. .......................... 514/212
4,920,101 * 4/1990 Minaskanian et al. .............. 514/212
4,959,365 * 9/1990 Francoeur ............................ 540/485

FOREIGN PATENT DOCUMENTS 0129284 12/1984 (EP) .................................... 540/485
0251425 1/1988 (EP) .................................... 540/485
1553309 9/1979 (GB) .................................... 540/485

OTHER PUBLICATIONS

"Toxicity Screening of N–Alkylazacycloheptan–2–One Derivatives in Cultured Human Skin Cells: Structure–Toxicity Relationship", *Journal of Pharmaceutical Sciences*, vol. 78, No. 9, Sep. 1989, by Maria Ponec et al. pp. 738–741.

Use of Human Keratinocyte and Fibroblast Cultures for Toxicity Studies of Toptically Applied Compounds, *Journal of Pharmaceutical Sciences*, vol. 79, No. 4, Apr. 1990, by Maria Ponec et al., pp. 312–316.

* cited by examiner

*Primary Examiner*—James H. Reamer
(74) *Attorney, Agent, or Firm*—Young & Thompson

(57) ABSTRACT

The invention relates to pharmaceutical compositions for topical application containing at least one physiologically active agent and an effective amount of 1-oleylazacycloheptan-2-one as the human or animal epithelial membrane permeability enhancer, to the application of such pharmaceutical compositions by means of locally contacting the skin or other membrane of the human or animal with the above composition and to the 1-oleylazacycloheptan-2-one compound per se.

7 Claims, 4 Drawing Sheets

IC50 AND ENHANCEMENTFACTOR (F) VERSUS CARBON NUMBER OF ALKYLCHAIN
+ IC50
o F
ENHANCEMENTFACTOR (F)
0
1
2
3
4
IC50 (mmol)
0.1
1
10
2
4
5
6
8
10
12
14
16
18
NUMBER OF CARBON ATOMS IN ALKYL CHAIN

Fig-4

PHARMACEUTICAL COMPOSITIONS CONTAINING 1-OLEYLAZACYCLOHEPTAN-2-ONE AS ENHANCING AGENT OF TRANSPORT ACROSS BIOLOGICAL MEMBRANES

BACKGROUND OF THE INVENTION

1. Field of invention

The invention relates in general to pharmaceutical compositions containing 1-oleylazacycloheptan-2-one in the function of human or animal epithelial membrane permeability enhancer. Furthermore the invention encompasses the use of above pharmaceutical compositions for the treatment of for instance inflammation as well as the compound per se.

2. Background of the prior art

One of the epithelial membranes of interest is the skin. More in particular the skin is frequently used as a portal of entry into the body for two classes of physiologically active agents: (I) systemically active agents, (II) locally active agents. For an increasing number of systemically active agents, delivery through the skin is favorable, since absorption kinetics can be controlled, and various side effects (such as hepatic first-pass metabolism) avoided.

For locally active agents, such as anti-inflammatory drugs, the skin is both the portal of entry and the target organ.

Generally, the greatest problem in applying physiologically active agents topically is that the skin is an effective barrier for penetration of such agents. The epidermis of the skin has an exterior layer of dead cells called the "stratum corneum" which is tightly structured, lipid rich and which provides an effective barrier against all kinds of agents whether used alone or in water or oil solution or suspension. However, once a physiologically active agent has penetrated the stratum corneum it can readily pass through the basal layer of the epidermis and into the dermis.

In the prior art many vehicle compositions are disclosed containing 1-substituted azacycloheptan-2-ones useful in enhancing penetration of the skin by physiologically active agents.

In British patent specification 1,553,309 a large number of 1-al-kylazacycloheptan-2-ones, in particular 1-n-dodecylazacycloheptan-2-one are disclosed. As indicated on page 1 of this British patent these compounds are found to be useful as vehicles for delivering physiologically active agents through body membranes such as the skin and for retaining these agents in body tissues. However, no details concerning the possible mode(s) of action of these 1-$C_{1-18}$ alkylazacycloheptan-2-ones are reported in this patent.

U.S. Pat. No. 3,989,816 discloses a method for enhancing the penetration of physiologically active agents through human and animal membranes e.g. the skin by administering to a human or animal membrane a composition comprising an effective amount of the active agent and a suitable amount of an 1-alkyl-azacycloheptan-2-one, the alkyl substituent having the formula —$(CH_2)$n—R, wherein R is selected from the group consisting of alkyl moieties having 1–18 carbon atoms and aryl groups, and n is 0 or a positive integer from 1–10. Preferably the alkyl substituent has 1–12 carbon atoms. However, the penetration enhancing properties of these compounds are considered inadequate.

Further U.S. Pat. No. 4,310,525 relates to the application of an effective amount of 1-dodecyl-azacycloheptan-2-one as the sole anti-inflammatory agent for treating inflammation in humans and animals. The active compound is used in the form of a composition applied topically on the human or animal skin. The concentration of 1-dodecylazacycloheptan-2-one in the -composition may vary from about 10 to 100% and preferably from about 42 to 80% by weight. According to this U.S. Pat. No. 4,310,525 the compound 1-dode-cyl-azacycloheptan-2-one per se is not used as penetration enhancer for physiologically active agents, but is, apparently, as such capable of temporarily reducing the signs and symptoms of inflammation.

EP-A-0 129 284 relates to topical pharmaceutical compositions containing a physiologically active agent and a binary combination of 1-dodecyl-azacycloheptan-2-one on the one hand and a specific $C_3$–$C_4$-diol or a 1-substituted azacycloalkyl-2-one on the other hand as penetration enhancing agents. However, the use of a mixture of specific membrane-penetration enhancing agents at specific ratio's is considered undesirable whereas nothing is disclosed about the possible toxic properties of these enhancer mixtures.

EP-A-0 251 425 discloses an article for the administration of physiologically active substances comprising a plasticized polyvinylchloride layer containing from about 20 to about 70% by wt. of a polyvinyl-chloride resin from about 20 to about 70 % of a plasticizer and from about 0.5 to 35% of the physiologically active substance. The plasticizer may be 1-dodecyl-azacycloheptan-2-one which in fact also acts as a membrane penetration enhancer for the physiologically active compound through the stratum corneum.

SUMMARY OF THE INVENTION

Surprisingly, it has been found by Applicant that the compound 1-oleylazacycloheptan-2-one as such is both a more potent enhancer for percutaneous absorption than the 1-alkylazacycloheptan-2-ones according to the prior art and less toxic than the 1-dodecylazacycloheptan-2-one, considered the preferred compound according to the above cited prior art.

Therefore, the invention relates to 1-oleylazacycloheptan-2-one per se, to compositions comprising at least one physiologically active agent and the penetration enhancer according to the invention, to devices such as skin patches containing such a composition and to a method for enhancing the penetration of active agents through human and animal epithelial membranes while applying the specific 1-alkyl-azacycloheptan-2-one derivative mentioned above.

BRIEF DESCRIPTION OF THE DRAWINGS

FIG. 4 is an electron microscopic picture of the stratum corneum subjected to a freeze-fracture replication procedure according to test 3 in the presence of 1-oleylazacycloheptan-2-one.

DETAILED DESCRIPTION OF THE INVENTION

Figure 1:
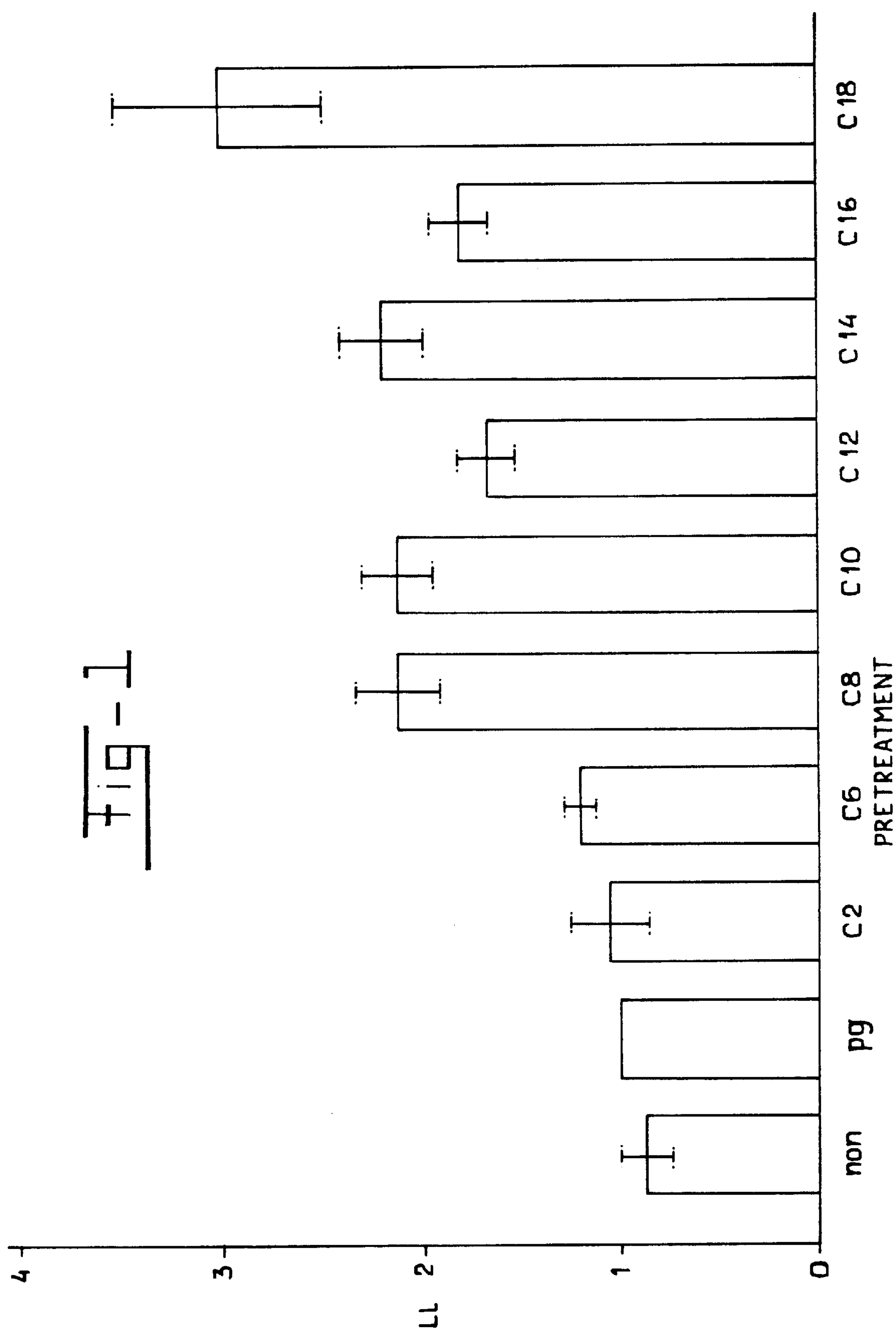
FIG. 1 is a graph showing the influence of the length of the alkyl chain of the 1-alkylazacycloheptan-2-ones on percutaneous nitro-glycerine transport enhancement (see test 1).

The compound described above is useful in relationship to percutaneous penetration i.e. the compound according to the invention enhances the percutaneous absorption of topically administered physiologically active agents, e.g. drugs, growth factors, radical scavengers, etc.

The compound according to the invention may be prepared, for example, by treating azacycloheptan-2-one with oleyl halide or preferably a relevant hydrocarbyl residue with an excellent nucleophilic leaving group, for example mesylate, tosylate, etc. in the presence of a base in an inert atmosphere. As a base sodium hydride may be used. The reaction is carried out under anhydrous conditions in e.g. a hydrocarbon solvent like dry toluene at room temperature or higher for a period of 1 or more hours. In this respect, it is emphasized that the compound according to the invention may also be prepared according to other methods known from the prior art for similar compounds.

The concentration of 1-oleylazacycloheptan-2-one, which may be used in the present invention, is an effective concentration for enhancing percutaneous absorption of active agents. Generally, this concentration ranges from 1 to about 95, and preferably from 5 to about 40% by wt. of the composition.

The compositions according to the invention comprise at least one physiologically active agent, e.g. an antibacterial agent, an antifungal agent, an active steroid, an antihistaminic agent, antihypertensives and other cardiovascular drugs, sex hormones, anti-diabetics, hypnotics, anti-parkinson drugs, local anaesthetics, anticoagulants, analgesics, antimigraine drugs. The physiologically active agents may be used at a safe and effective level in the compositions according to the invention, being in general from about 0.01% to about 30% by weight of the composition. However, levels outside this range may also be used.

Examples of antibacterial agents which may be used in this invention include penicillins, cephalosporins, penicillinase, erythromycins, tetracyclines, chloramphenicols, streptomycins, etc.

Examples of antifungal agents i.e. fungistatic and fungicidal agents are thiabendazole, chloroxine, amphotericin, candicidin, fungimycin, etc.

Examples of steroids which may be used with the 1-oleylazacycloheptan-2-one include corticosteroids such as e.g. cortisone, cortodoxone, prednisone, etc. Examples of retinoids such as retinoic acid may also be used.

Dosage forms for topical application may include solutions, nasal sprays, lotions, ointments, cremes, gels, suppositories, sprays, aerosols as well as devices such as skin patches, bandages and dressings containing a composition according to the invention. Typical conventional pharmaceutical carriers which make up the foregoing dosage forms include water, acetone, isopropylalcohol, ethylalcohol, polyvinylpyrrolidone, propylene glycol, fragrances, gel-producing materials, mineral oil, stearyl alcohol, steric acid, spermaceti, sorbitan monoleate, "Polysorbates", "Tweens", etc.

The amount of the composition and thus of the physiologically active agent therein, to be administered will obviously be an effective amount for the desired result expected therefrom. This, of course, will be ascertained by the ordinary skill of the practitioner. Due to enhanced activity which is achieved with the enhancer, the dosage of the active agent may often be decreased from that generally applicable.

As used herein the term "topical" is intended to include application to all external membrane barriers including the cutaneous or epidermis regions and the mucous membranes including the gastrointestinal tract, the respiratory tract and the genitourinary tract.

Experimental

The potent membrane enhancer properties of 1-oleylazacycloheptan-2-on may be derived from a series of different experiments according to which the compound according to the invention is compared to 1-alkylazacyclopheptan-2-ones known from the prior art.

The series of different experiments comprise four tests:

1. Skin transport kinetics;
2. Differential thermal analysis;
3. Freeze-fracture electron microscopy; and
4. In vitro skin cell toxicity screening, i.e. the collagen contraction test.

Test 1

Skin Transport Kinetics

Human stratum corneum samples (18 mm in diameter) were obtained from fresh human skin (abdomen) by trypsinization. The stratum corneum samples were firstly prehydrated at 95% relative humidity (RH) over a saturated disodium hydrogen phosphate solution, then either submerged for 24 hours at 34° C. with 200 microliter of a 10% solution of an alkyl-aza-cycloheptan-one in propylene glycol by topical application, or directly used for a diffusion study.

The stratum corneum samples were subsequently sandwiched between silastic sheetings (127 micrometer thick silicone membranes, Dow Corning) which have been proven not to control the transport rate of the model drug used in the study, nitroglycerin. The thus obtained sandwiches were clamped in two-chamber flow-through diffusion cells and subjected to 24 hours diffusion experiments. The donor compartment having a volume of 16$\mu$l was flushed with a 0.05% nitroglycerin solution at a pumping rate of 35 ml/hr. A saturated disodium hydrogen phosphate solution was pumped at a rate of 5 ml/hr through the acceptor chamber having a volume of 16$\mu$l. Fractions of the acceptor fluid were collected at 1 hour intervals, and nitroglycerin was detected using a reversed phase HPLC procedure (chrom-sphere $C_{18}$ 100×30 mm column eluted at 22° C. (methanol:water=1:1) at a 1.1 ml/min flow rate (Spectroflow 400, Kratos.). The absorbance at 201 nm of the effluent was monitored on Waters 450 var. wavelength detector).

Test 2

Differential Thermal Analysis (DTA)

For differential thermal analysis human stratum corneum samples were pretreated (after prehydration) by submersion in the in test 1 described enhancer solutions for 24 hours, using untreated prehydrated stratum corneum samples as controls. Differential thermal analysis of ca. 20 mg samples was then performed on a differential scanning calorimeter (Maple).

Test 3

Freeze-fracture Electron Microscopy

For freeze-fracture electron microscopy stratum corneum samples were pretreated during 24 hours with solutions of azacycloheptanones in propylene glycol by applying about 200 microliter per $cm^2$ of the solution on the apical surface. Samples were then snapfrozen in melting nitrogen (method according to Umrath, J. Microsc. 101: 103 (1974)), cross-fractured (Holman et al., J. Invest. Dermatol, 94: 332 (1990)

)in a Balzers Freeze Fracture apparatus (Balzers 400 BAF) at high vacuum. The fracture surfaces were then shadowed with Pt and overcast with a layer of carbon. Upon thawing, the samples were cleaned to obtain the surface replicas. These were scooped up on copper grids and examined in a transmission electron microscope (Philips 401, operated at 80 kV).

Test 4

Collagen Contraction Test

Skin toxicity tests were performed using the so-called collagen contraction test (Ponec et al. Journal of Pharmaceutical Sciences Vol. 78, No. 9, September 1989 and Vol. 79, No. 4, April 1990). In this test collagen sheets containing human dermal fibroblasts are subjected to a challenge by toxic agents (in this case the 1-alkylazacycloheptan-2-ones) and the resulting inhibition of the contraction, normally induced by the collagenase released by the fibroblasts, is measured as a function of time. The concentration of the agent, at which the shrinkage is 50% of the control, is taken as the IC50, the "50% inhibition level". The out-come of this test proved to be highly comparable to both fibroblast- and human epidermal keratinocyte growth inhibition tests.

RESULTS

Re Test 1

From the kinetical results summarized in table 1 below it is quite clear that the oleyl derivative is by far the most potent enhancer with respect to nitroglycerin transport.

TABLE 1

Effects of alkyl chainlength of azone derivatives (1-alkylazacycloheptan-2-one derivatives) on the penetration of nitroglycerine through stratum corneum at 33° C.

| treatment | flux ± SD $\mu$g/h/cm$^2$ | N | $R_{sc}$ ± SD $10^3$* s/cm | $P_{sc}$ ± SD $10^{-5}$* cm/s | F |
|---|---|---|---|---|---|
| none | 7.05 ± 1.05 | 3 | 233.5 ± 46 | 0.45 ± 0.07 | 0.87 ± 0.13 |
| propylene-glyc. | 8.11 ± 1.00 | 3 | 200.0 ± 25 | 0.55 ± 0.06 | 1.00 |
| C2 | 9.20 ± 1.60 | 4 | 169.0 ± 34 | 0.59 ± 0.12 | 1.05 ± 0.20 |
| C6 | 10.6 ± 0.25 | 3 | 142.0 ± 4 | 0.70 ± 0.02 | 1.20 ± 0.08 |
| C8 | 14.3 ± 1.45 | 3 | 102.0 ± 13 | 0.99 ± 0.13 | 2.13 ± 0.21 |
| C10 | 14.0 ± 0.70 | 3 | 105.0 ± 7 | 0.96 ± 0.06 | 2.13 ± 0.18 |
| C12 | 11.3 ± 0.50 | 3 | 133.0 ± 9 | 0.75 ± 0.05 | 1.67 ± 0.15 |
| C14 | 14.4 ± 1.20 | 3 | 100.0 ± 10 | 1.00 ± 0.10 | 2.20 ± 0.21 |
| C16 | 12.2 ± 0.50 | 3 | 123.0 ± 6 | 0.81 ± 0.04 | 1.80 ± 0.15 |
| C18 | 18.1 ± 3.30 | 3 | 74.0 ± 18 | 1.35 ± 0.32 | 3.00 ± 0.51 |

pretreatments were performed with 10% enchancer in propyleneglycol, Cx denotes the length of the alkyl chain of the azone; C18 stands for oleyl.
N = number of stratum corneum samples tested
$P_{sc}$ = the permeability coefficient through stratum corneum, calculated and corrected for the contribution of the silastic sheeting.
$P_{sc}$ = J/Cd, the steady state drug flux through the stratum corneum (= J), divided by the donor concentration (= Cd).
$R_{sc}$ = the resistance coefficient for stratum corneum, calculated and corrected for the contribution of the silastic sheeting, i.e. obtained by substracting the silastic sheeting contribution from the total resistance of the sandwich (= $1/P_{sc}$).
F = factor of comparison, the socalled 'Enhancement Factor'.

Re Test 2

Figure 2:
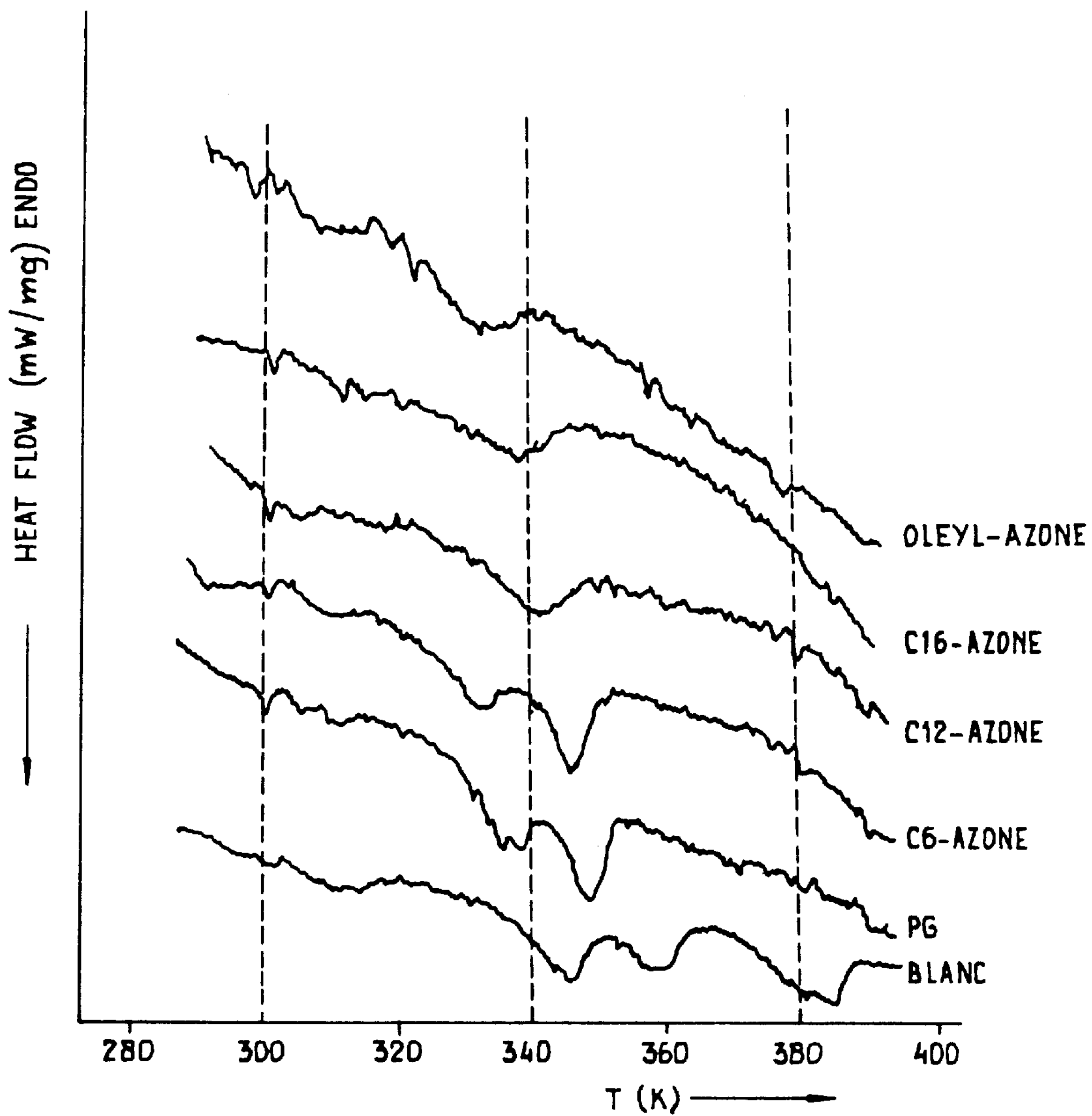
FIG. 2 is a graph showing the influence of the length of the alkyl chain of the 1-alkylazacycloheptan-2-ones on the thermal behaviour of human stratum corneum.

The DTA results (FIG. 2) show that oleyl azone strongly influences both the gel-liquid transition temperature of the intercellular lipids, and the corresponding transition enthalpy. (3.3 J.g-1 vs. 7 J.g-1 of the control). It is pointed out that the change in enthalpy is especially meaningful, and would correspond to a large degree of acyl chain disorder in the lipid bilayers in the inter-cellular space in the stratum corneum. This would then strongly enhance the overall permeability of the tissue.

Re Test 1

The electron microscopic results show, that especially the oleyl azone preparation penetrates deeply into the stratum corneum and induces the separation of a non-lamellar phase, which looks much less structured than the endogeneous lamellar lipid phase, and should therefore be more permeable (FIG. 4).

Re Test 4

Figure 3:
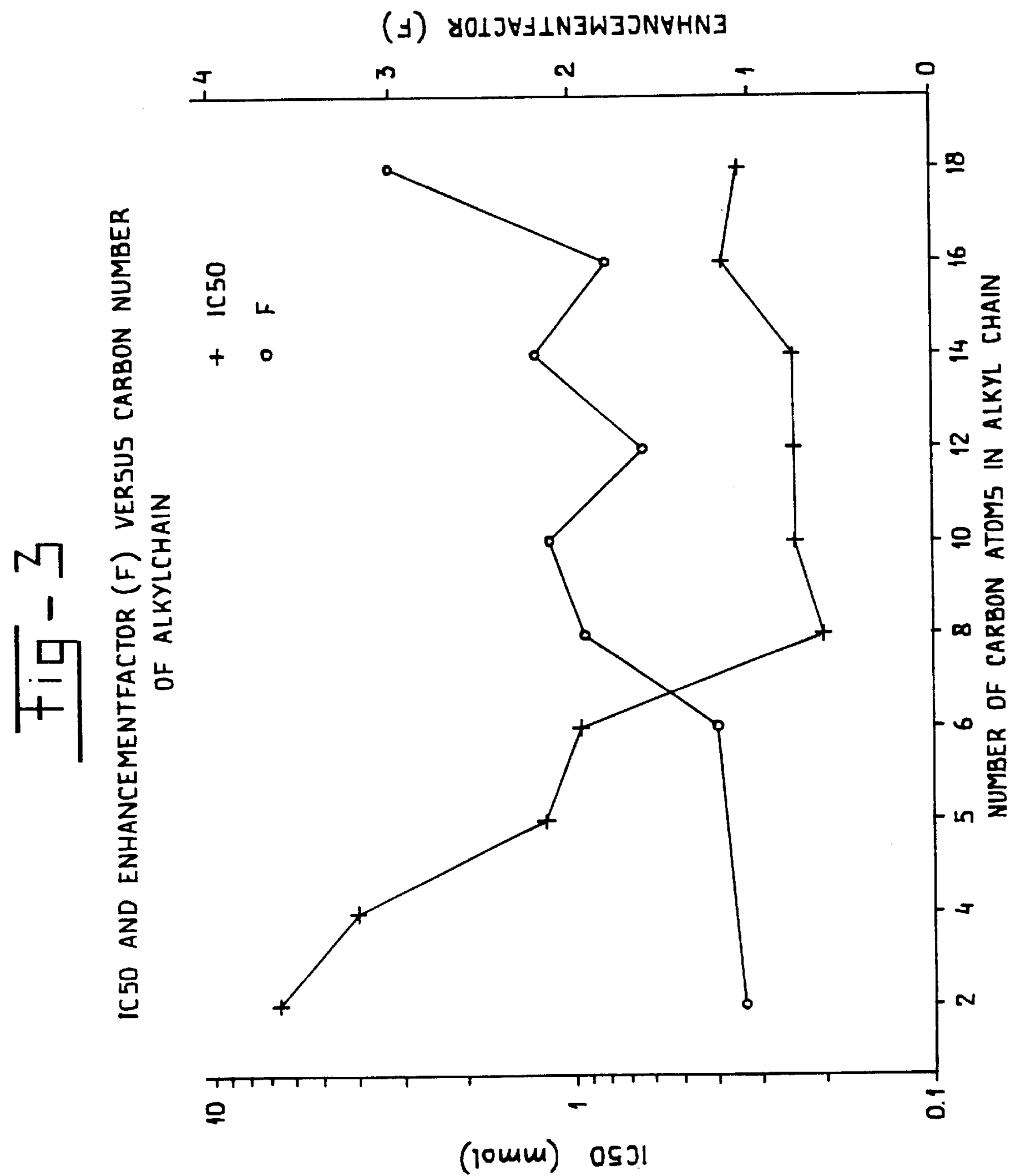
FIG. 3 is a graph showing the IC50-values and enhancement factors of the 1-alkylazacycloheptan-2-ones tested in relationship to the length of the alkyl chain in these compounds.

The toxicity tests (FIG. 3) indicate that oleyl azone is almost the least toxic azone among the effective enhancers (from C10 up to C18), and less toxic than C12 azone (IC50 0.8 mM vs. 0.24 mM).

Summarized it can be stated that the compound (1-oleyl-azacyclo-heptan-2-one) is a new, effective, moderately toxic penetration enhancer.

What is claimed is:

1. 1-Oleyl-azacycloheptan-2-one.

2. A composition comprising at least one physiologically active agent and an effective amount of 1-oleylazacycloheptan-2-one as a human or animal epithelial membrane permeability enhancing agent.

3. The composition according to claim 2, wherein the physiologically active agent is selected from the group consisting of antibacterial agents, antifungal agents, active steroids, retinoids, antihistaminic agents, radical scavengers, antihypertensives and other cardiovascular drugs, sex hormones, anti-diabetics, hypnotics, anti-parkinson drugs, local anaesthetics, anticoagulants, analgesics and antimigraine drugs.

4. The composition according to claim 1, wherein the 1-oleyl-azacycloheptan-2-one is present in a concentration ranging between 1–95% by weight, preferably 5–40% by weight.

5. A method for enhancing the penetration of a physiologically active agent through human and animal epithelial membranes comprising the application on a human or animal membrane of a composition having an effective amount of said agent and an effective membrane permeability enhancing amount of 1-oleylazacycloheptan-2-one.

6. The method according to claim 5, wherein the physiologically active agent is selected from the group consisting of antibacterial agents, antifungal agents, active steroids, retinoids, antihistaminic agents and radical scavengers, antihypertensives and other cardiovascular drugs, sex hormones, anti-diabetics, hypnotics, anti-parkinson drugs, local anaesthetics, anticoagulants, analgesics and antimigraine drugs.

7. Devices like (trans)dermal patches, bandages and dressings comprising a layer containing a composition according to claim 2.

* * * * *